US011160678B2

(12) United States Patent
Waldsich

(10) Patent No.: US 11,160,678 B2
(45) Date of Patent: Nov. 2, 2021

(54) MEDICAL, IN PARTICULAR ORTHOPAEDIC, AID

(71) Applicant: medi GmbH & Co. KG, Bayreuth (DE)

(72) Inventor: Bettina Waldsich, Bayreuth (DE)

(73) Assignee: Medi GmbH & Co. KG, Bayreuth (DE)

( * ) Notice: Subject to any disclaimer, the term of this patent is extended or adjusted under 35 U.S.C. 154(b) by 0 days.

(21) Appl. No.: 16/169,748

(22) Filed: Oct. 24, 2018

(65) Prior Publication Data

US 2019/0125017 A1    May 2, 2019

(30) Foreign Application Priority Data

Oct. 26, 2017  (EP) .................................... 17020502

(51) Int. Cl.
| | | |
|---|---|---|
| *A61F 5/01* | (2006.01) | |
| *A41D 31/04* | (2019.01) | |
| *A61F 13/08* | (2006.01) | |
| *A61F 13/00* | (2006.01) | |
| *A61F 5/00* | (2006.01) | |

(Continued)

(52) U.S. Cl.
CPC ............ *A61F 5/01* (2013.01); *A41D 13/1254* (2013.01); *A41D 31/04* (2019.02); *A61F 5/00* (2013.01); *A61F 5/0109* (2013.01); *A61F 13/00063* (2013.01); *A61F 13/08* (2013.01); *A41D 13/0543* (2013.01); *A41D 2400/26* (2013.01); *A41D 2400/28* (2013.01)

(58) Field of Classification Search
CPC .... A61N 2005/0645; A61N 2005/0661; A61N 5/0616; A61N 2005/063; A61N 2005/0662; A61N 5/06; A61N 2005/0615; A61N 2005/0657; A61F 5/01; A61F 13/08; A61F 13/00063; A61F 5/0109; A61F 5/00; A41D 2400/28; A41D 31/00; A41D 31/02; A41D 2400/10; A41D 2400/26; A41D 13/00; A41D 2400/32; A41D 31/04; A41D 13/1254; A41D 13/0543
See application file for complete search history.

(56) References Cited

U.S. PATENT DOCUMENTS

| | | | | |
|---|---|---|---|---|
| 5,883,740 A | * | 3/1999 | Chubb | ..................... A41D 1/00 359/350 |
| 6,017,360 A | * | 1/2000 | Chubb | .................. A41D 7/006 607/88 |

(Continued)

FOREIGN PATENT DOCUMENTS

| | | |
|---|---|---|
| DE | 19724518 A1 | 12/1998 |
| DE | 202008005286 U1 | 6/2008 |

(Continued)

*Primary Examiner* — Robert H Muromoto, Jr.
(74) *Attorney, Agent, or Firm* — Rimôn, P.C.

(57) ABSTRACT

A medical, in particular orthopaedic, aid (1, 1', 1"), such as for example an orthosis (1), bandage (1') or compressive item of clothing (1"), consisting of at least one base body (2, 2', 2") of at least one elastic and/or non-elastic textile material (3, 3', 3"), which is designed for the supporting of tissue and/or parts of the body of a patient, wherein the at least one textile material (3, 3', 3") of the base body (2, 2', 2") is designed at least partially to be substantially transmissible with respect to UV radiation.

25 Claims, 2 Drawing Sheets

Figure 1:
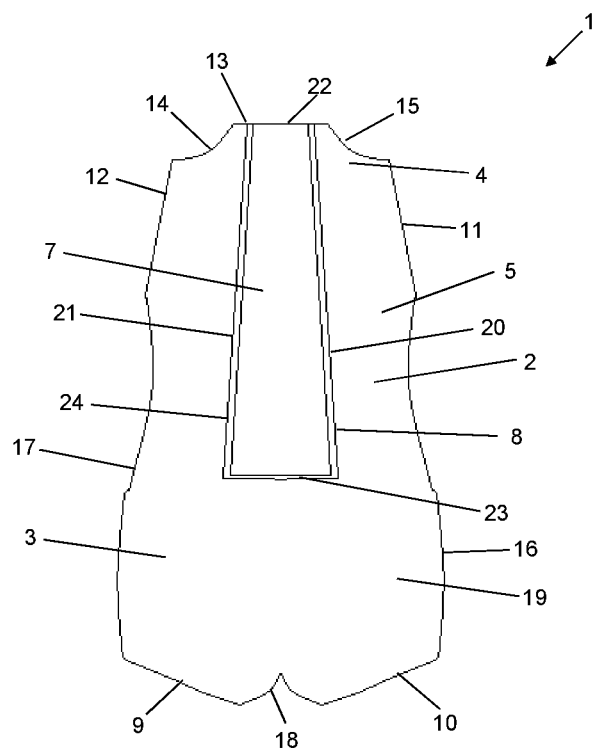

(51) Int. Cl.
*A41D 13/12* (2006.01)
*A41D 13/05* (2006.01)

(56) References Cited

U.S. PATENT DOCUMENTS

| | | | | |
|---|---|---|---|---|
| 6,861,658 | B2* | 3/2005 | Fiset | A61N 5/0614 250/365 |
| 8,084,377 | B2* | 12/2011 | Kreindel | A41D 31/00 442/131 |
| 8,327,669 | B2* | 12/2012 | Weihermueller | D04B 1/106 66/172 E |
| 8,476,172 | B2* | 7/2013 | Christof | D04B 1/16 442/2 |
| 8,512,268 | B2* | 8/2013 | Weihermueller | A61F 5/0106 602/20 |
| 8,540,781 | B2* | 9/2013 | Nissels | A61F 2/66 623/55 |
| 8,602,961 | B2* | 12/2013 | Schmidt | A61K 31/198 600/15 |
| 8,845,567 | B2* | 9/2014 | Herresthal | A61F 13/062 602/26 |
| 9,955,742 | B2* | 5/2018 | Lopez | A41D 31/00 |
| 10,292,443 | B2* | 5/2019 | Lopez | A41D 31/00 |
| 10,299,526 | B2* | 5/2019 | DuCasse | A42B 1/067 |
| 10,322,297 | B1* | 6/2019 | Hinds | A61N 5/0616 |
| 10,344,408 | B2* | 7/2019 | Herold-Herrmann | A41B 11/121 |
| 10,494,747 | B2* | 12/2019 | Atmanspacher | D04B 1/26 |
| 2002/0108405 | A1* | 8/2002 | Yakopson | A61F 13/08 66/177 |
| 2002/0129434 | A1* | 9/2002 | Rabinowicz | A41C 3/0014 2/69 |
| 2003/0094019 | A1* | 5/2003 | Miyake | D04B 21/16 66/195 |
| 2003/0130603 | A1* | 7/2003 | Minne | A41D 13/0531 602/19 |
| 2007/0287613 | A1* | 12/2007 | Adducci | A61B 17/135 482/111 |
| 2010/0061796 | A1* | 3/2010 | Kurth | A61F 2/76 403/66 |
| 2011/0040222 | A1* | 2/2011 | Weihermueller | A61F 5/0106 602/5 |
| 2011/0083475 | A1* | 4/2011 | Weihermueller | D04B 1/106 66/170 |
| 2011/0144768 | A1* | 6/2011 | Kremser | A61F 2/5046 623/33 |
| 2011/0160631 | A1* | 6/2011 | Herresthal | A61F 5/0109 602/26 |
| 2011/0284729 | A1* | 11/2011 | Abouraddy | G01J 1/04 250/227.11 |
| 2012/0035519 | A1* | 2/2012 | Thelemann | A61F 5/03 602/19 |
| 2012/0046760 | A1* | 2/2012 | Nissels | A61F 2/66 623/55 |
| 2012/0165596 | A1* | 6/2012 | Schmidt | A61K 31/198 600/15 |
| 2013/0084777 | A1* | 4/2013 | Starr | A41C 3/0057 450/86 |
| 2014/0057234 | A1* | 2/2014 | Nink-Grebe | G09B 23/28 434/262 |
| 2014/0162531 | A1* | 6/2014 | Mazourik | A41C 3/0028 450/86 |
| 2015/0089709 | A1* | 4/2015 | DuCasse | A42B 1/067 2/69 |
| 2015/0102208 | A1* | 4/2015 | Appelboom | G06F 19/3481 250/208.2 |
| 2015/0177423 | A1* | 6/2015 | Scipioni | A41D 13/005 136/257 |
| 2017/0079341 | A1* | 3/2017 | Lopez | A41D 31/00 |
| 2018/0043179 | A1* | 2/2018 | Solis Herrera | A61N 5/0618 |
| 2018/0242666 | A1* | 8/2018 | Lopez | A41D 31/00 |
| 2019/0076082 | A1* | 3/2019 | Poutiatine | A61B 5/441 |
| 2019/0298583 | A1* | 10/2019 | Hoffeins | A41B 11/123 |

FOREIGN PATENT DOCUMENTS

| | | |
|---|---|---|
| EP | 0604601 B1 | 9/1995 |
| EP | 1284695 B1 | 2/2003 |
| EP | 2954879 A1 | 12/2015 |

* cited by examiner

MEDICAL, IN PARTICULAR ORTHOPAEDIC, AID

CROSS-REFERENCE TO RELATED APPLICATIONS

This application claims priority to European Patent Application serial no. 17020502.5 filed Oct. 26, 2017, the contents of which is incorporated herein by reference in its entirety as if set forth verbatim.

The present invention relates to a medical, in particular orthopaedic, aid such as for example a bandage, orthosis or compressive clothing item, in particular for patients with osteoporosis, according to the claims, and to a medical, in particular orthopaedic, unit according to the claims.

Such medical, in particular orthopaedic, aids serve in particular to support, relieve, immobilize, guide and/or protect tissue and/or parts of a patient's body. Bandages, for example, are manufactured specifically for various parts of the body, such as e.g. knee, elbow, hand joints and are worn in the case of inflammation, injury or preventively, in order to conserve, support the corresponding joints or to protect these from further injury or from stress which is too great.

Compressive clothing items, in particular clothing items worn on the legs, such as for example socks, stockings or tights, serve in particular in a targeted manner to exert pressure onto the body of a patient. The aim is to relieve a damaged venous and/or lymphatic system of a patient. For the formation of the said medical aids, in particular of bandages and compression stockings, preferably so-called compressive knitted fabrics are used, which are knitted flat or in a circular manner by means of a flat or circular knitting machine.

Orthoses are used to stabilize, relieve, immobilize, guide and/or correct limbs or the torso of patients. In particular the latter plays an important role in the treatment of osteoporosis, in which through the decrease in bone density, a deformation of the spinal column and therefore malpositions of the intervertebral joints, malfunctions of the tendons, ligaments and musculature is brought about, which results in disabilities in everyday life.

Such a back orthosis for straightening the spinal column is known for example from EP 1 284 695 B1.

The known orthosis permits a straightening of the spinal column and therefore of the patient's upper body by the modelling of a special back splint of the orthosis to the curved spinal column, which therefore lies against the back from the rear. For this, the orthosis itself is constructed as a normal clothing item, in particular as an orthopaedic clothing item, with an elongate pocket, open at the top and bottom, to receive the rigid splint, held closely, elastically or with slight play therein, supporting the spinal column. The base body of the orthosis is preferably constructed for this as an orthopaedically indicated one-piece undergarment, which consists of cotton or synthetic fibre material and has various stretch zones which have a tension in the state when being worn.

Furthermore, orthoses for the treatment of osteoporosis are known, which in addition to a splint supporting the spinal column, in place of a normal item of clothing, have fastening straps which are guided in the manner of backpack straps.

In addition to the treatment of osteoporosis by means of orthoses, it is known, furthermore, to prevent or alleviate osteoporosis by means of medicaments rich in vitamin D. Magnesium and vitamin D are responsible for calcium to be received from food and incorporated into bone. Calcium is one of the most important building blocks of human bone. However, so that the calcium can arrive into the bones at all, vitamin D is essential.

All the medical aids known hitherto aim merely one therapeutic treatment, in particular the supporting, relieving, immobilizing, guiding and/or protecting of tissue and/or parts of a patient's body. The prevention of the pain or respectively diseases which are to be treated is not supported by the medical aid, but rather takes place, for example in the case of osteoporosis, by the intake of medicaments, in particular of vitamin D preparations.

It proves to be disadvantageous here that various inconveniences are connected with the intake of medicaments. On the one hand, the medicaments must be purchased, i.e. the patient has an expenditure in terms of finance and time. On the other hand, the patient must have the medicament constantly available, because intake must take place regularly.

The natural supplying with vitamin D does not basically take place via food, but rather via the sun. Through direct solar irradiation onto the skin, the body itself can produce vitamin D. However, one's own production of vitamin D is impeded by clothing the human body with garments and medical aids which are impervious to light, such as orthoses or bandages for example. Consequently, an intake of corresponding medicaments is necessary for the production of vitamin D.

Sunlight-transmissible textile materials and clothing items are in fact known from the prior art, for example from EP 0 604 601 B1, however these are only designed to be used in the field of swimwear. They therefore serve a different purpose, namely the tanning of the skin while areas of the wearer's body are covered. They are not suitable or designed for use in medical, in particular orthopaedic, aids, in particular for supporting, relieving, immobilizing, guiding and/or protecting tissue and/or parts of a patient's body.

The known textile material is designed to be substantially transmissible with respect to the UV radiation leading to the tanning of the skin. The stitch opening width, therefore the size of the stitch opening, is responsible for the UV transmissibility. The thread diameter and the thread density are critical here. In order to further improve the transmissibility, in addition a honeycomb-like structure is proposed with stitch opening rows which extends in angularly offset directions. In addition, it is proposed to print the textile material with contrasting fluorescent colours, so that the material is opaque when lying on the skin.

Furthermore, it is known for example from DE 197 24 518 A1 that by means of chemical band filters the UV transmissibility, in particular the transmissibility of UV-A and UV-B radiation is able to be adjusted variably in the sun protection fibres, in particular in the sun protection textiles. This textile material is also designed for use as suntanning clothing.

Elastic and/or non-elastic textile materials or respectively clothing items which are designed for the supporting of tissue and/or of parts of a patient's body, in particular compressive knitted fabrics which, in addition to a compressive effect, also have a transmissibility with respect to UV radiation, are not known from the prior art. Different demands are made on these textile materials for the production of medical compression than on commercially available textile materials which are used inter alia for the swimwear field. The supporting and compression effect of these materials is many times greater.

The present invention is based on the problem of providing a medical, in particular orthopaedic, aid which avoids the disadvantages of the prior art, in particular in addition to a supporting, relieving, immobilizing, guiding and/or protecting of tissue and/or parts of a patient's body, is designed at the same time for the prevention of vitamin D deficiency.

According to an example embodiment of the medical, in particular orthopaedic aid, such as for example as a bandage, orthosis or compressive clothing item, in particular for patients with osteoporosis, this consists of at least one base body of at least one elastic and/or non-elastic textile material, which is designed for the supporting of tissue and/or of parts of a patient's body, wherein the at least one textile material of the base body is designed in addition at least partially for the prevention of vitamin D deficiency, therefore at least in some areas so as to be transmissible with respect to UV radiation.

According to a second example embodiment of the medical, in particular orthopaedic aid, the textile material of the base body is designed to be substantially transmissible with respect to the UV-B radiation of sunlight responsible for vitamin D production, and substantially non-transmissible with respect to the UV-A radiation of sunlight which is harmful to the skin.

Preferably, the textile material of the base body has, in sections, different transmissibilities of UV radiation. Preferably, the base body comprises at least a second textile material which is designed so as to be less, or not transmissible with respect to UV radiation.

According to a third example embodiment, the first and/or the at least one second textile material of the base body of the medical aid is designed to be substantially opaque. Hereby, it is possible to wear the aid at the same time, therefore in addition to the therapeutic treatment, as an item of clothing for the covering of parts of the body.

The first and/or the at least one second textile material of the base body itself is preferably formed from a knitted, warp-knitted or woven fabric. In the case of a designing of the textile material as a knitted fabric, this is preferably a compressive knitted part which is manufactured by means of a flat or circular knitting machine and has a compression thread which is worked into a base knitted fabric as a weft thread or in a stitch-forming manner. The knitted part, through the different integrating of the weft thread into the base knitted fabric and/or through the different design of the base knitted fabric, for example through the different number of stitches per stitch row, preferably has a graduated compression profile in the longitudinal direction of the knitted fabric. In particular with the design of the base knitted fabric as a compression stocking, also designated a support stocking, a graduated compression profile is advantageous.

So that the at least one textile material, in particular the compressive knitted fabric, of the base body of the bandage, orthosis or of the compressive item of clothing, is transmissible with respect to UV radiation, it is proposed to use a yarn, in particular fibres, transmissible with respect to UV radiation. Here, preferably the material of the yarn, therefore the fibres, is transmissible with respect to UV radiation or the surface of yarn or respectively of the fibres is modified such that a knitted fabric produced with the yarn is transmissible with respect to UV radiation. The textile construction, therefore the intermediate spaces of the yarn, and/or the transmission of the UV radiation through the fibres, therefore the fibre type, is namely responsible for the transmissibility of the UV radiation. With the use of a UV-transmissible material it is proposed in particular to design the yarn, which for the production of the compressive effect preferably consists of a highly elastic thread core, in particular of an elastane, which is wound around by one or several threads, so as to be transmissible with respect to UV radiation. Here, in particular, the at least one wind-around thread, in particular its fibres, and/or the thread core, is transmissible with respect to UV radiation. In the case of these compressive knitted fabrics, which are also preferably formed having several layers, the formation of the UV-transmissibility through the structure, therefore through the stitch width, as is known from the swimwear field with very thin textiles, is rather more unsuitable, because the compressive effect of the knitted fabric draws it together very intensively and thereby very few intermediate spaces are present. Alternatively, the UV-transmissibility can of course also be achieved through the combination of a UV-transmissible woven fabric structure and one or more UV-transmissible yarns.

According to a further example embodiment, the medical aid has at least one functional element, which is able to be connected detachably or non-detachably to the base body. The functional element here is preferably a support belt, a pelotte, an orthopaedic splint, in particular a back splint, or a connecting device for the detachable positioning of the base body on a patient. A connecting device is understood to mean preferably a plug-in, locking or hook and loop fastener connection.

According to a further example embodiment, in addition to the textile material of the base body, the functional element for the additional therapeutic treatment is also designed at least partially to be substantially transmissible with respect to UV radiation. For this, the functional element is preferably made from a material which is substantially transmissible with respect to UV radiation. Alternatively, a structural solution, for example a porous structure of the functional element, is also possible.

To receive the functional element in the base body of the medical aid, the base body has at least one pocket which is configured such that for example at least one orthopaedic splint is able to be received therein. For this, the pocket is preferably mounted on the inner or outer side of the base body, in particular sewn on or welded on, or alternatively thereto, is worked into the base knitted fabric, for example knitted in.

According to a further example embodiment, the base body is designed so as to be sock- or stocking-shaped. For this, it preferably has a knitted fabric, in particular a compressive knitted fabric. The base body is therefore designed as a stocking, in particular a half stocking, or sock. Alternatively, the sock- or stocking-shaped base body can also be a component part of an orthosis or bandage, in particular a foot bandage.

Here, preferably one or more functional elements, such as for example one or more support straps, pelottes, splints and/or connecting devices are fastened to the base body.

According to a further example embodiment, the base body is designed in the form of a one-piece undergarment, in particular a so-called bodysuit, preferably for the treatment of osteoporosis. In combination with a special back splint, this serves to straighten the spinal column and therefore the upper body of a patient. The base body is preferably manufactured here from a knitted fabric or from a woven fabric, such as for example cotton or synthetic fibre material, and has various stretch zones.

According to an example embodiment of a medical, in particular orthopaedic, unit, the latter has a medical, in particular orthopaedic, aid according to one of the preceding example embodiments and an item of clothing, in particular an item of clothing for the upper body or an item of clothing for the legs, which is also designed to be substantially transmissible with respect to UV radiation, in particular with respect to UV-B radiation. The item of clothing for the upper body is preferably designed here as a shirt, long-sleeved shirt or, for example, as a pullover. The item of clothing for the legs can comprise trousers, inter alia tights, trousers with short or long leg pieces, or swimming trunks.

The present medical aid is distinguished by a range of considerable advantages.

Through the design of the base body from a textile material which is designed at least partially to be substantially transmissible with respect to UV radiation, at the same time in addition to a supporting, relieving, immobilizing, guiding and/or protecting of tissue and/or parts of a patient's body, a prevention of vitamin D deficiency is made possible.

Through the transmissibility of UV radiation, therefore of the direct irradiation, in particular of sunlight, onto the skin of a patient, the body itself can produce vitamin D. For the production of vitamin D, therefore, no intake of corresponding medicaments is necessary. Hereby, the user is not obligated to purchase corresponding medicaments. He therefore has no further, in particular additional, financial expenditure. On the contrary, he can utilize the sunlight, available without cost, for the production of vitamin D.

A further advantage which is connected therewith is the elimination of the expenditure of time connected with the intake of the medicaments, and the requirement to constantly have the medicaments available. Both facilitate the therapeutic treatment of a patient with disorders, in particular with osteoporosis. Also, high-dosed vitamin D regimens, which are necessary in the case of an acute vitamin D deficiency, because conventional doses are not sufficient, in order to rapidly rectify a vitamin D deficiency, are avoided.

The possibility, at the same time in addition to supporting, relieving, immobilizing, guiding and/or protecting tissue and/or parts of a patient's body, of tanning the skin of a patient forms a further advantage of the invention. Through the transmissibility of the natural UV radiation, in particular of the UV-B radiation of sunlight responsible for the tanning of the skin, a tanning effect also occurs at locations of the skin of a patient's body on which the aid according to the invention is worn. The medical aid can therefore be worn in particular during leisure activities, such as sunbathing for example, without causing undesired marks on the skin.

The invention is explained below with the aid of several example embodiments and in connection with the enclosed drawings.

Figure 2:
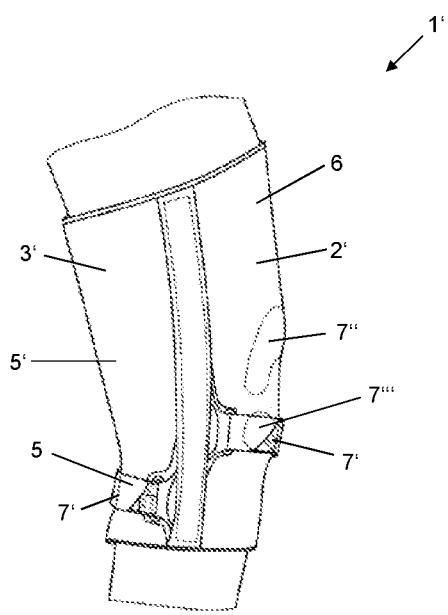
Figure 3:
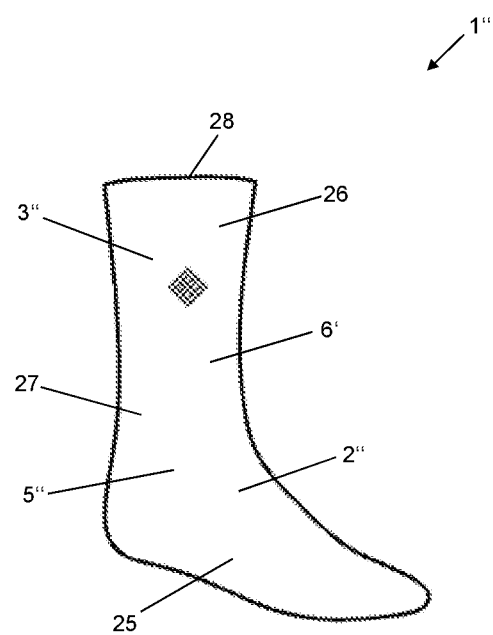

There are shown here:

FIG. 1 a first example embodiment of the medical, in particular orthopaedic, aid in the form of a one-piece undergarment, in particular as a so-called bodysuit, for the treatment of osteoporosis, FIG. 2 a second example embodiment of the medical, in particular orthopaedic, aid, in the form of a bandage, in particular a knee bandage, FIG. 3 a third example embodiment of the medical, in particular orthopaedic, aid, designed as a stocking, in particular compression stocking, in order to relieve a damaged venous and/or lymphatic system or a stressed muscle structure of a patient.

The medical, in particular orthopaedic, aid illustrated in FIG. 1, is a bodysuit 1, designed in the form of a one-piece undergarment, for the treatment of osteoporosis. This is cut like a conventional bodysuit. It has several openings, namely openings 9, 10 for the legs, openings 11, 12 for the arms, and opening 13 for the head or respectively the neck of a patient. At the edges 14, 15, 16, 17 and 18, the body 1 is closed. The regions 14, 15 and 18 can alternatively also be designed to be opened. On its rear side 19, the bodysuit 1 has a pocket 8 running along the spinal column, in order to receive a functional element 7, in particular an orthopaedic splint, which preferably extends from a coccygeal region, particularly preferably from a sacral region, up to a cervical region. The pocket 8 is preferably closed at the sides 20, 21 and at the upper end 22. At the lower end 23 an opening is situated, through which the splint 7 is able to be received in the pocket 8. Alternatively, the pocket 8 can also have a lateral opening. According to the shape of the splint, for example with a widening 24 at its lower end, the pocket 8 is adapted thereto. In order to hold the very flat splint 7, modelled so as to be fitting against the spinal column of the patient, on the bodysuit 1 in the pocket 8, a fastening means can be provided for this, for example a hook and loop fastener or press-stud, preferably at the opening 23 of the pocket 8. On the front side, which is not shown, the bodysuit 1, like conventional bodysuits or jackets, has an opening which is able to be closed by means of a zip fastener or by means of press-studs. For this, the opening preferably extends centrally from an upper end of the bodysuit into a lower region.

Furthermore, for the supporting and relieving of tissue and parts of a patient's body, in particular the spinal column, the bodysuit 1, in particular its base body 2 made from a woven fabric 5, preferably has one or more stretch zones, in particular designed so be of different intensity, which are formed by differently elastic textile material 3, wherein for stiffening, several textile layers can be present one over another. Alternatively, the bodysuit 1 can also be made from an, in particular compressive, knitted fabric or warp-knitted fabric, which is designed for the supporting of tissue and/or parts of a patient's body. The compressive knitted fabric is characterized in that, in addition to one or more stitch-forming base knit threads, it contains at least one worked-in, preferably inserted, weft thread.

The compressive woven fabric or knitted fabric of the bodysuit 1 is preferably made from an opaque fabric, which is designed to be substantially transmissive with respect to UV radiation. The textile material of the bodysuit 1 is preferably designed such that it is substantially transmissive with respect to UV-B radiation of sunlight, responsible for the production of vitamin D, and is substantially non-transmissive with respect to the UV-A radiation of the sunlight which is harmful to the skin.

The functional element 7, namely the back splint, is preferably also made from a material which is substantially transmissive with respect to UV radiation, for example from UV-transmissive acrylic glass or respectively plexiglass, in order to achieve inter alia also a tanning effect at sites of the skin of a patient's body on which the functional element 7 is worn, owing to the transmissibility of the UV-B radiation of the sunlight responsible for the tanning of the skin.

In order, in particular, to prevent sunburn, due to the transmissibility of the UV-B radiation of the sunlight, responsible for the tanning of the skin, of the bodysuit 1 on the patient's skin, the bodysuit 1 can furthermore preferably have different transmissibilities of UV radiation in sections. For this, for example, the regions of the bodysuit 1 which are particularly exposed to the solar radiation, such as for example the regions which cover the shoulders of the user, are designed to be less to non-transmissive with respect to UV radiation. For this, these regions can be made from a second textile material 4, which is designed to be non-transmissive with respect to UV radiation.

In FIG. 2 a second example embodiment of the medical, in particular orthopaedic, aid is shown, in the form of a bandage, in particular a knee bandage 1'. The knee joint bandage 1' comprises here an elastic base body 2' with a functional element, in particular a pelotte 7", running over the patellar tendon in the position when worn. In order to be able to exert sufficiently great pressure onto the tendon, the knee joint bandage 1" preferably has, in addition to the pelotte 7" which is preferably formed detachably from the base body 2', further functional elements, namely tension straps 7' and connecting devices 7'". The tension straps 7" are preferably connected non-detachably to the base body 2'. A first tension strap runs on the front side only partially around the base body 2'. A second tension strap is provided on the rear side and offset in height with respect to the first tension strap on the knee joint bandage 1'. This strap also runs only partially around the base body 2'.

The base body 2' is preferably made from a knitted fabric 5', in particular an opaque flat- or circular-knitted and compressive knitted fabric, which is designed for the supporting of tissue and/or parts of a patient's body and so as to be substantially transmissive with respect to UV radiation. The knitted fabric 5' is preferably also designed such that it is substantially transmissive with respect to UV radiation of sunlight responsible for the production of vitamin D, and substantially non-transmissive with respect to the UV-A radiation of sunlight which is harmful to the skin.

The functional elements, namely the tension straps 7' and the pelotte 7" are preferably also made from a material which is substantially transmissible with respect to UV radiation. Here, the tension straps 7' are preferably made from a woven fabric 5 which is transmissible with respect to UV radiation. The pelotte 7" preferably consists of a UV-transmissible synthetic material body.

In FIG. 3 the medical, in particular orthopaedic, aid is designed as a stocking, in particular a compression stocking 1'", consisting of a compressive knitted part 5", in order to relieve a damaged venous and/or lymphatic system of a patient. The compression stocking 1", designed in one piece in this example embodiment, consists of a foot part 25 and calf part 26. Alternatively, it is also conceivable that the parts 25, 26 are able to be connected detachably to one another. The foot part 25 is designed to cover the sole, the instep, the malleolus and the ankle 27 of a user. The calf part 26 at least partially surrounds the calf region of a user, in order for example to exert pressure onto the calf musculature pump. The compression stocking 1" is preferably assigned to one of the standardized four compression classes by means of the compression values of the sock- or respectively stocking-shaped base body 2" in the ankle region 27. For this, the stocking 1" preferably has a weft thread in every second knitted stitch row. In the ankle region, the stocking 1" has the highest compression values. In the direction of the upper end 28 of the calf part 26, the compression stocking 1" has a graduated, in particular decreasing, compression profile. The stocking 1" itself preferably consists of a knitted part 5", in particular of a compressive knitted part 6', which is preferably formed from at least one stitch-forming base knit thread and at least one compression thread, in particular inserted weft thread.

In this example embodiment, also, the base body 2", namely the stocking 2", is made from a textile material which is substantially transmissive with respect to UV radiation. The compressive knitted part 6' here is substantially transmissive with respect to UV radiation at least partially, therefore at least at one or more sites of the stocking. For this, it is proposed to design the stitch size or the structure of the knitted part 6' such that the compressive knitted part 6' is substantially transmissive with respect to UV radiation. Alternatively, as known from the prior art, suitable thread material can also be used, which additionally is substantially transmissive with respect to UV-B radiation of sunlight responsible for the production of vitamin D, and substantially non-transmissive with respect to the UV-A radiation of sunlight which is harmful to the skin. Also in this example embodiment, the base body 2" is substantially opaque. Alternatively, however, this can also be designed to be transparent, at least in some areas.

The invention is not restricted to the described example embodiments, but rather comprises all embodiments which apply or contain the fundamental, corresponding functional principle of the invention. Furthermore, all the features of all the described and illustrated example embodiments are able to be combined with one another.

The invention claimed is:

1. An orthosis (1) for patients with osteoporosis, consisting of a bodysuit with at least one base body (2, 2', 2") formed of at least one first elastic and/or non-elastic textile material (3, 3', 3"), which has a pocket (8) and two or more tension straps adapted to wrap at least partially around a portion of the base body in a manner that straightens the upper body of a patient when the orthosis is worn by the patient, wherein the orthosis (1) has at least one functional element (7, 7', 7", 7'") which is an orthopaedic splint and which is able to be detachably or non-detachably connected to the base body (2, 2', 2"), characterized in that the at least one elastic and/or non-elastic textile material (3, 3', 3") of the base body (2, 2', 2"), the pocket, and the two or more tension straps are designed at least partially to be substantially transmissible with respect to UV radiation.

2. The orthosis (1) according to claim 1, characterized in that the at least one first elastic and/or non-elastic textile material (3, 3', 3") of the base body (2, 2', 2") is designed to be substantially transmissive with respect to UV-B radiation of sunlight which is responsible for the production of vitamin D, and to be substantially non-transmissible with respect to the UV-A radiation of the sunlight which is harmful to the skin.

3. The orthosis (1) according to claim 1, characterized in that the textile material (3) of the base body (2) has, in sections, different transmissibilities of UV radiation.

4. The orthosis (1) according to claim 1, characterized in that the base body (2) comprises at least one second textile material (4) that is designed to be less or non-transmissible with respect to UV radiation.

5. The orthosis (1) according to claim 4, characterized in that the first elastic and/or non-elastic textile material and/or the at least one second textile material (3, 3', 3"; 4) of the base body (2, 2', 2") is designed to be substantially opaque.

6. The orthosis (1) according to claim 4, characterized in that the at least one second textile material (3, 3', 3"; 4) of the base body (2, 2', 2") is formed from a woven fabric (5), knitted fabric (5, 5') or warp-knitted fabric.

7. The orthosis (1) according to claim 6, characterized in that the compressive knitted part (6') has a graduated compression profile.

8. The orthosis (1) according to claim 1, characterized in that the functional element (7, 7', 7", 7'") is designed to be substantially transmissible with respect to UV radiation.

9. The orthosis (1) according to claim 1, characterized in that the functional element is a back splint or a connection device (7'") for the detachable positioning of the base body (2') on a patient.

10. The orthosis (1) according to claim 1, characterized in that the base body (2) has at least one pocket (8), which is designed such that at least one orthopaedic splint (8) is able to be received therein.

11. The orthosis (1) according to claim 1, characterized in that the base body (2) is designed in the form of a one-piece undergarment.

12. A medical unit having the orthosis (1) according to claim 1, and an item of clothing designed to be substantially transmissible with respect to UV radiation, in particular with respect to UV-B radiation.

13. The orthosis (1) according to claim 1, wherein at least one first elastic and/or non-elastic textile material is formed of a yarn having fibres that are transmissible with respect to UV radiation.

14. The orthosis (1) according to claim 6, wherein the first elastic and/or non-elastic textile material and/or the at least one second textile material is/are formed from several layers of the woven fabric (5), several layers of the knitted fabric (5, 5') or several layers of the warp-knitted fabric.

15. The orthosis (1) according to claim 1, characterized in that the bodysuit is comprised of at least one first elastic and/or non-elastic textile material having different transmissibilities of UV radiation in one or more sections, wherein the one more sections comprise at least one first region designed to be less to non-transmissive with respect to UV radiation, and at least one second region designed to be more transmissive with respect to UV radiation compared with the first region.

16. The orthosis (1) according to claim 1, characterized in that the bodysuit is comprised of several layers of at least one first elastic and/or non-elastic textile material (3, 3', 3").

17. The orthosis (1) according to claim 15, characterized in that the bodysuit is comprised of several layers of at least one first elastic and/or non-elastic textile material (3, 3', 3").

18. The orthosis (1) according to claim 15, characterized in that the at least one first region and/or the at least one second region is/are comprised of several layers of at least one first elastic and/or non-elastic textile material (3, 3', 3").

19. Use of the orthosis (1) according to claim 1 to straighten the upper body of a patient, comprising donning the orthosis (1) and applying two or more tension straps at least partially around a portion of the base body in a manner that straightens the upper body of the patient.

20. The use according to claim 19, wherein the orthosis (1) is donned under clothing worn by the patient.

21. The use according to claim 20, wherein the clothing is designed to be substantially transmissible with respect to UV radiation.

22. The use according to claim 19, wherein the orthosis (1) is donned over clothing worn by the patient.

23. The use according to claim 22, wherein the clothing is designed to be substantially transmissible with respect to UV radiation.

24. A method of treating osteoporosis in a patient, comprising donning the orthosis (1) of claim 1 and applying two or more tension straps at least partially around a portion of the base body in a manner that straightens the upper body of the patient.

25. A method of treating osteoporosis in a patient, comprising donning an orthosis by the patient, wherein the orthosis comprises at least one base body formed of at least one first elastic and/or non-elastic textile material, which base body is characterized by a pocket adapted to hold an orthopaedic splint, a region adapted to cover at least a portion of the shoulders of the patient, and two or more tension straps adapted to wrap at least partially around a portion of the base body in a manner that straightens the upper body of a patient when the orthosis is worn by the patient, characterized in that the at least one elastic and/or non-elastic textile material of the base body, the pocket, the region, and the two or more tension straps are designed at least partially to be substantially transmissible with respect to UV radiation.

* * * * *